(12) United States Patent
Hoheisel et al.

(10) Patent No.: US 6,823,039 B2
(45) Date of Patent: Nov. 23, 2004

(54) COMPUTED TOMOGRAPHY APPARATUS ALSO EMPLOYABLE FOR X-RAY DIAGNOSTIC EXAMINATIONS

(75) Inventors: Martin Hoheisel, Erlangen (DE); Hartmut Sklebitz, Erlangen (DE)

(73) Assignee: Siemens Aktiengesellschaft, Münich (DE)

(*) Notice: Subject to any disclaimer, the term of this patent is extended or adjusted under 35 U.S.C. 154(b) by 0 days.

(21) Appl. No.: 10/176,275

(22) Filed: Jun. 20, 2002

(65) Prior Publication Data
US 2003/0002626 A1 Jan. 2, 2003

(30) Foreign Application Priority Data
Jun. 20, 2001 (DE) .......................................... 101 29 764

(51) Int. Cl.[7] .................................................. A61B 6/03
(52) U.S. Cl. ............................ 378/19; 378/4; 378/98.8
(58) Field of Search ............................. 378/98.8, 4, 11, 378/13, 19, 22, 190, 65, 98.9

(56) References Cited

U.S. PATENT DOCUMENTS

| 4,093,864 | A | * | 6/1978 | Hahn et al. .................. 378/152 |
| 5,055,821 | A | * | 10/1991 | Keller et al. ........... 340/286.01 |
| 5,448,610 | A | * | 9/1995 | Yamamoto et al. ........... 378/19 |
| 5,454,022 | A | * | 9/1995 | Lee et al. .................. 378/98.8 |
| 6,067,342 | A | * | 5/2000 | Gordon ....................... 378/19 |
| 6,181,769 | B1 | * | 1/2001 | Hoheisel et al. ........... 378/98.8 |
| 6,198,790 | B1 | | 3/2001 | Pflaum |
| 6,304,627 | B1 | | 10/2001 | Horbaschek |
| 6,453,009 | B2 | * | 9/2002 | Berezowitz et al. ........ 378/118 |

FOREIGN PATENT DOCUMENTS

DE  19921280 C1 * 11/2000  ............ A61B/6/03

* cited by examiner

Primary Examiner—Edward J. Glick
Assistant Examiner—Chih-Chieng Glen Kao
(74) Attorney, Agent, or Firm—Schiff Hardin LLP

(57) ABSTRACT

A computed tomography apparatus has a gantry with an X-ray source and an x-ray detector, and at least one further, curved solid-state radiation detector that is movable into and out of the beam path of the x-ray source is provided in the gantry.

15 Claims, 2 Drawing Sheets

COMPUTED TOMOGRAPHY APPARATUS ALSO EMPLOYABLE FOR X-RAY DIAGNOSTIC EXAMINATIONS

BACKGROUND OF THE INVENTION

1. Field of the Invention

The present invention is directed to a computed tomography apparatus of the type having a gantry with an X-ray source and an X-ray detector thereon.

2. Description of the Prior Art

In practice, it is increasingly necessary in examination of a patient with a computed tomography apparatus to implement X-ray diagnostic examinations, for example in the form of fluoroscopy examinations, digital radiography or digital subtraction angiography, without time delay and without repositioning the patient. To this end, it is advantageous to provide an additional X-ray detector that is irradiated in the course of these types of examinations, which supplies corresponding signals. As little structure as possible, in the already complicated structure of the computed tomography apparatus should be modified for this purpose. In particular, the employment of a second X-ray source should be avoided and the examination in the gantry should ensue without large displacement paths of the patient support. The gantry is the scanner unit of the apparatus that rotates around the patient wherein the X-ray source and the X-ray detector are arranged. One conceivable solution would be to arrange the additional X-ray detector in the beam path preceding the X-ray detector employed, in the course of standard CT examinations. Since, however, the additional X-ray detector would absorb a considerable part of the incident X-rays, this approach would involve the disadvantage of a greatly increased patient dose. Such an arrangement thus is not an acceptable solution. Due, further, to the planar implementation of the X-ray detector, that already can be employed only as a flat detector given arrangement thereof in the gantry, the X-ray detector employed for the CT examination—which is implemented as a curved array—would have to be offset considerably toward the outside in order to be able to provide an additional detector at all, with a given gantry diameter. This involves significant design disadvantages, particularly an increased support ring diameter for the rotating parts, which would lead to significantly larger centrifugal forces.

Known combination systems that, thus, allow standard computed tomography examinations as well as X-ray diagnostics have an additional X-ray tube and a separate detector that are employed together for the x-ray diagnostics. It is also known to employ a patient bed with built-in detector panel from which signals for the x-ray diagnostics signals are supplied.

U.S. Pat. No. 6,198,790 discloses such an X-ray diagnostics apparatus with a computed tomography system that has a first X-ray tube secured to a live ring that emits a fan-shaped payload ray beam and a detector array lying thereopposite. A second X-ray tube is secured to the live ring at a right angle relative to the first X-ray tube, a matrix-shaped X-ray detector being arranged at the live ring lying opposite the second X-ray tube.

U.S. Pat. No. 6,304,627 discloses an X-ray diagnostic installation wherein an exposure unit has a radiation transmitter and a line detector lying opposite one another that are rotatable around an exposure region. A support mechanism with a support plate for the examination subject also is provided. The X-ray diagnostic installation has a further radiation receiver allocated to it that, proceeding from a standby position, can be adjusted into an exposure position for receiving an X-ray beam emanating from the radiation transmitter of the computed tomography apparatus.

SUMMARY OF THE INVENTION

An object of the present invention is to provide a computed tomography apparatus that eliminates the initially described disadvantages and allows the implementation of X-ray diagnostic examinations in the gantry of the computed tomography apparatus.

This object is achieved in accordance with the invention in a computed tomography apparatus of the type initially described that has at least one further, curved solid-state radiation detector in the gantry that can be moved out of the beam path of the X-ray source.

The invention employs a displaceably seated solid-state radiation detector in the gantry that is curved, so that it can be introduced as needed into the gap between the inner ring of the gantry and the X-ray detector adjacent thereto, that is likewise curved and serves for the actual CT exposure, so that the displaceably seated solid-state detector is positioned in the beam path of the X-ray source that is already present. Due to the curvature, the extremely small available space can be advantageously utilized. Additionally, nothing about the structure of the gantry needs to be changed, insofar as the actual CT X-ray radiation detector need not be radially offset farther toward the outside due to the curvature of the solid-state radiation detector. A curved solid-state radiation detector can be manufactured using an adequately thin, and thus flexible, detector carrier.

The inventive computer tomography apparatus thus allows switching from the actual CT examination to an x-ray diagnostic examination by means of a simple, as needed introduction of the additional solid-state radiation detector without time delay and without patient repositioning, with the same X-ray tube being employed for both examination modes. All of this is possible without excessive modifications of the actual gantry structure, since the existing, extremely small available space is optimally utilized due to the curved embodiment.

It is especially advantageous, due to the arrangement of the additional X-ray detector for x-ray diagnostics within the gantry, that, by a suitable rotation of the gantry, the examination can ensue in any arbitrary transillumination direction that is most expedient for the desired diagnosis. This enables a manipulation that is just as flexible as a C-arm, which would not be the case for an additional X-ray detector built into the patient bed.

As described, it is expedient when the solid-state radiation detector can be positioned in front of the X-ray detector, i.e. can be introduced into the gap between inner gantry ring and the CT X-ray detector.

Inventively, the bending radius r of the detector should be in the range $r \geq a$ and $r \geq b/2$, whereby a is the spacing of the X-ray detector from the X-ray source and b is the inside diameter of the gantry.

In an embodiment of the invention the solid-state radiation detector is movable into the beam path by displacement along a circular path around the rotational axis of the gantry. In this embodiment, thus, the solid-state radiation detector is quasi-tangentially inserted into the beam path along the circular path proceeding from the side. Expediently, the rotational axis around which the circular path displacement motion ensues coincides with the rotational axis of the gantry.

In an embodiment of the invention, an alternative the solid-state radiation detector can be moved into the beam path by axial displacement parallel to the rotational axis of the gantry. Which motion alternative is selected is ultimately dependent on the nature of the space relationships in the gantry and, in particular, on how large the solid-state radiation detector itself is. In any case, suitable displacement and guide means, for example slide or glide rails, on which the solid-state radiation detector is seated and guided are provided for the movement of the solid-state radiation detector, is a suitable drive, for example in the form of a servo motor or motor actuator or the like. It is important that these motion and drive components are as small as possible so that they do not require an unnecessarily large amount of space.

In a further embodiment of the invention, the electronic components serving for the drive and the readout of the pixels of the solid-state radiation detector are not arranged at the front edge of the solid-state radiation detector ("front" being with reference to the motion direction upon introduction into the beam path). This embodiment is advantageous because the structural height of the curved solid-state radiation detector can be kept low in the region of the front, introduction edge, so that the solid-state radiation detector can be introduced into a gap between the inside gantry ring and the x-ray detector that is narrower than the actual structural height of the curved solid-state radiation detector, including the electronic components arranged at the edge side. These components are expediently arranged at the other three longitudinal edges of the detector at that side facing toward the outside gantry ring.

Due to the curvature of the solid-state radiation detector, it is expedient for the size of the pixels of the solid-state radiation detector to decrease toward the straight edge of the curved solid-state detector. Further, the pixel position, i.e. the position of the rows and columns, can be adapted in tangential and axial directions so that—with reference to a flat panel—no or only a small amount of distortion and/or pixel anisotropy occur.

Further, a cable-free transmission system for transmitting the signals picked up by the solid-state radiation detector to a control device arranged externally of the gantry, and for the reception of control signals by this control device, can be provided. This transmission system can be an optical transmission system, particularly an IR transmission system, or an electromagnetic transmission system in the form of antennas or the like. Expediently, the transmission devices of the CT X-ray detector that are already present should be used, since these are present anyway, and providing additional transmission and reception means is avoided in this way.

Alternatively to the use of an optical or electromagnetic transmission and reception system, a stationary wiper ring and wiper contacts wiping interacting therewith can be provided for the transmission of signals from the solid-state radiation detector to the control device external from the gantry, and for the transmission of corresponding control signals.

As stated, the CT X-ray detector is in fact relatively long but is also very narrow, for which reason the ray field of the X-ray source is likewise narrow. Since the curved solid-state radiation detector serving for the x-ray diagnostics is essentially rectangular and clearly wider, it is necessary that the ray field can be appropriately varied for the utilization of the entire detector area. To this end, a diaphragm device allocated to the X-ray source is provided, this being controllable via the control device, so that the gating of the ray field can be varied in a simple and fast way dependent on the examination to be implemented. The same is true of the variation of the X-ray dose or of the amplitude of tube voltage and tube current, which are likewise controllable for variation via the control device dependent on the examination to be implemented, and thus on the detector to be irradiated.

DESCRIPTION OF THE PREFERRED EMBODIMENTS

Figure 1:
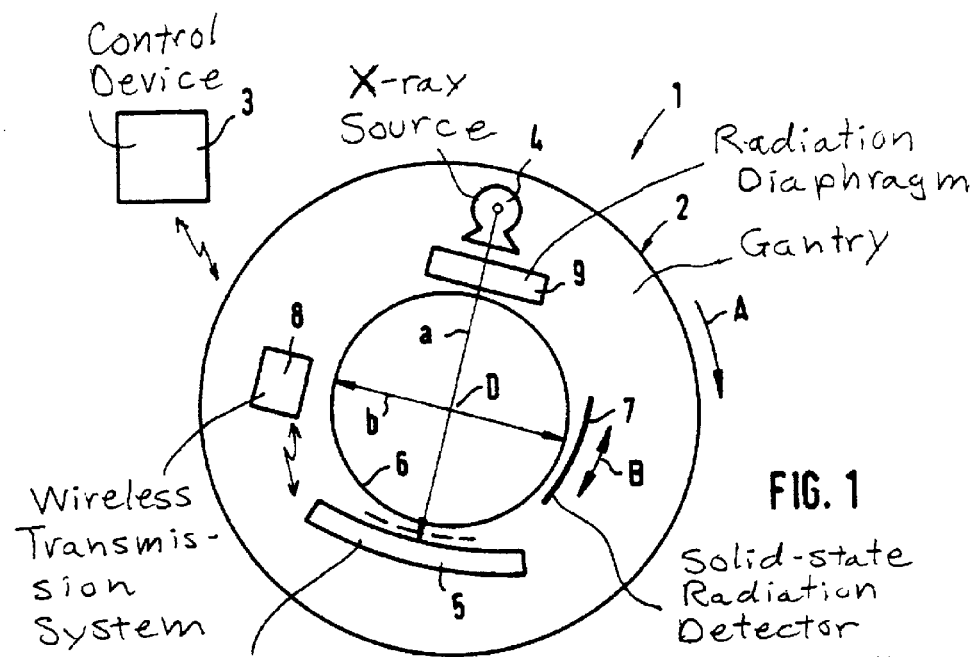
FIG. 1 is a schematic diagram of an inventive computed tomography apparatus with a curved solid-state radiation detector introducible into the beam path along a circular path.

FIG. 1 shows an inventive computed tomography apparatus 1, only the gantry 2 as well as a control device 3 thereof being shown for clarity. The gantry 2 is rotatable around a rotational axis D along the arrow A. The basic structure and operation of such a computed tomography apparatus are well known and need not be discussed herein.

An X-ray source 4 as well as an X-ray detector 5 lying there opposite are provided in the gantry 2. This X-ray detector 5 serves for the exposure of the actual CT images of a patient (not shown) inserted into the inner annular space that is limited by the inner ring 6 of the gantry 2.

A solid-state radiation detector 7 also is shown, this being curved and being displaceable along a circular path around the rotational axis D by drive and guide components (not shown in detail), as indicated by the double arrow B.

As shown with broken lines, this solid-state radiation detector 7 co-rotates with the gantry 2 and can be inserted into the beam path of the X-ray source 4 and be positioned in front of the X-ray detector 5. Standard X-ray diagnostics can be undertaken with this solid-state radiation detector 7, with the radiation of the X-ray source 4 that is already present being utilized in such diagnostics. Insofar as the solid-state radiation detector 7 is not needed, it is moved into a lateral standby position wherein it no longer lies in the beam path, so that the CT X-ray detector 5 can be irradiated as usual.

As stated, the solid-state radiation detector 7 is curved. Its bending radius is smaller than or equal to the spacing of the focus of the X-ray source 4 from the X-ray detector 5—referenced a in FIG. 1—and is greater than or equal to half the inside diameter of the gantry or of the inner gantry ring 6—the inside diameter being referenced b in FIG. 1.

A transmission and reception system 8 to be employed in common for the X-ray detector 5 and the solid-state radiation detector 7 also is shown. The registered signals of the respectively employed detector 5 or 7 can be transmitted to the control device 3 via the system 8, control signals that relate to the detectors 5 or 7 can be received via the system 8.

Further, a diaphragm device 9 that is placed in front of the X-ray source 4 is provided. The ray field can be varied in size using this diaphragm device 9, so that it can be adapted to the shape of the respectively employed detector 5 or 7 and the latter can be optimally irradiated (exposed).

Figure 2:
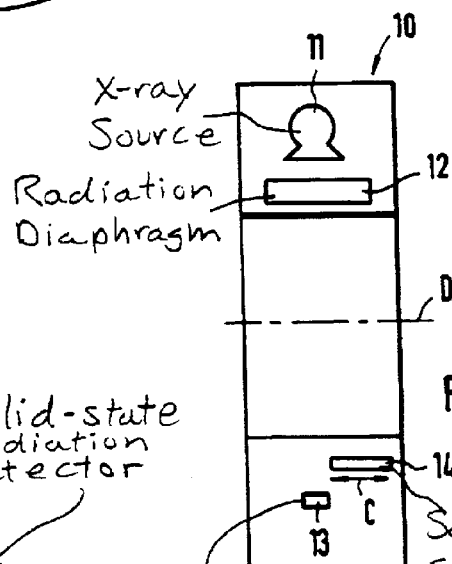
FIG. 2 is a sectional view through a gantry of an inventive computed tomography apparatus in a second embodiment with an axially displaceable, curved solid-state radiation detector.

In a schematic diagram, FIG. 2 shows a further embodiment of an inventive computed tomography apparatus 10. Here as well, a common X-ray source 11 with an allocated diaphragm device 12 and a CT X-ray detector 13 are utilized. The curved solid-state radiation detector 14 that is likewise provided here, however, is introducible into the beam path of the X-ray source 11 axially, and thus parallel to the rotational axis D in this embodiment, as indicated by the double arrow C.

Figure 3:
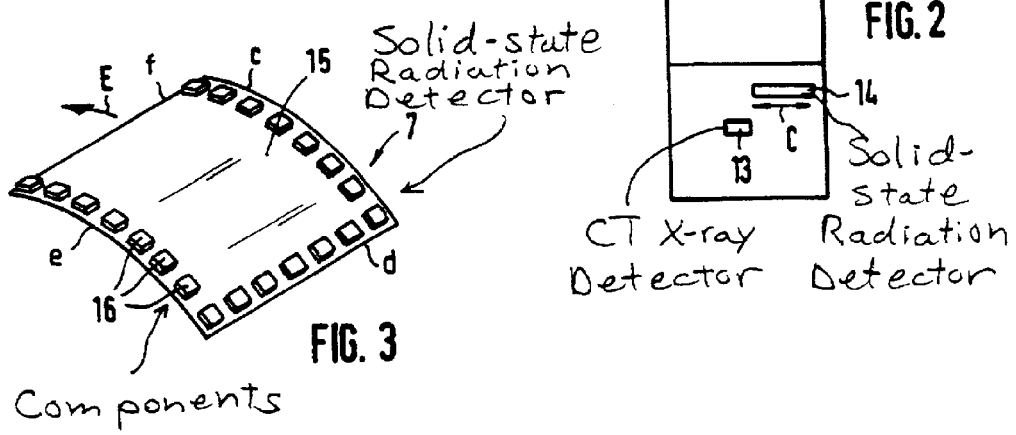
FIG. 3 a plan view onto a curved solid-state radiation detector in accordance with the invention.

In a schematic diagram, FIG. 3 shows a view of the curved solid-state radiation detector 7 from FIG. 1. As can be seen, electronic components 16 that are situated on the detector surface 15 and serve for the drive and readout of the individual pixels of the solid-state radiation detector 7 are arranged only at the edges c, d and e of the detector surface 15. No components 16 are provided at the edge f, which is the front edge with reference to the insertion direction of the detector 13 into the beam path (shown with the arrow E), so that the structural height of the detector 13 is significantly smaller in this region and it can be unproblemmatically inserted into the very narrow gap between the inner gantry ring 6 and the radiation detector 5.

Given the solid-state radiation detector 14 of the computer tomography apparatus 10, the components at either the edge c or e would not be present but would be present at the edge f since this solid-state radiation detector 14 is axially inserted into the beam path, whereby one of the curved edges c or e represents the front, introduction edge.

Figure 4:
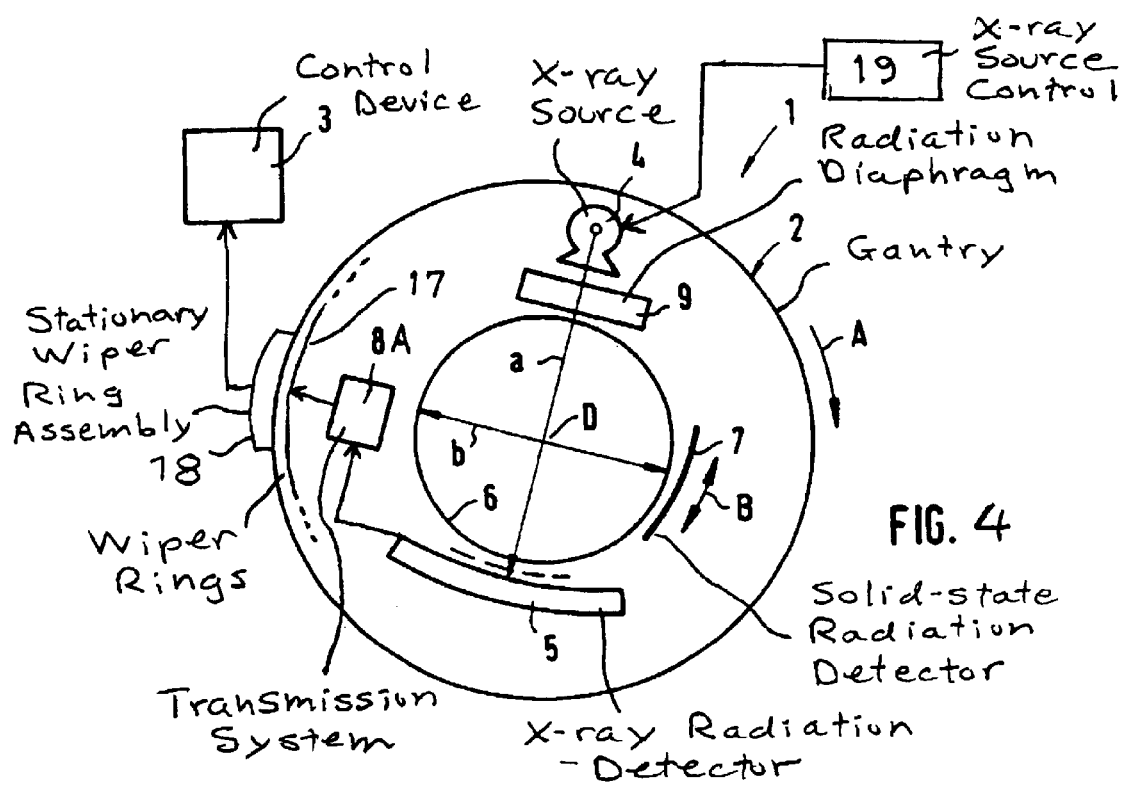
FIG. 4 is a schematic diagram of a further embodiment of an inventive computed tomography apparatus with a curved solid-state radiation detector introducible into the beam path along a circular path.

As shown in the embodiment of FIG. 4 instead of wireless transmission as in the embodiment of FIG. 1, signals from the X-ray radiation detector 5 can be transmitted via a hardwired transmission system 8A to wiper rings 17 disposed at the circumference of the gantry 2. The wiper rings 17 extend around the entirety of the circumference of the gantry 2, but only a portion of the wiper rings 17 is schematically shown in FIG. 4. The rotating wiper rings 17 interact with a stationary wiper ring assembly 18, from which signals are supplied to the control device 3.

FIG. 4 also shows an X-ray source control 19, that controls the X-ray source 4 independently of whether the X-ray beam is incident on the X-ray detector 5 or the curved solid-state radiation detector 7.

Although modifications and changes may be suggested by those skilled in the art, it is the intention of the inventors to embody within the patent warranted hereon all changes and modifications as reasonably and properly come within the scope of their contribution to the art.

We claim as our invention:

1. A computed tomography apparatus comprising:
   a rotatable gantry;
   an x-ray source mounted on said gantry which emits an x-ray beam proceeding along a beam path;
   an x-ray detector mounted on said gantry in said beam path, said x-ray source and said x-ray detector being rotatable by said gantry around an examination volume for obtaining signals from said x-ray detector for generating a tomogram; and
   a curved, solid-state radiation detector mounted in said gantry in addition to said x-ray detector, said curved, solid-state radiation detector being movable into and out of said beam path.

2. A computed tomography apparatus as claimed in claim 1 wherein said curved, solid-state radiation detector is mounted in said gantry so as to be movable in front of said x-ray detector.

3. A computed tomography apparatus as claimed in claim 1 wherein said curved, solid-state detector has a bending radius r, with $r \geq a$ and $r \geq b/2$, wherein a is a spacing between said x-ray detector and said x-ray source, and wherein b is an inside diameter of said gantry.

4. A computed tomography apparatus as claimed in claim 1 wherein said solid-state radiation detector is mounted in said gantry to be movable into said beam path by displacement along a circular path proceeding around a rotational axis of said gantry.

5. A computed tomography apparatus as claimed in claim 4 wherein said circular path has a rotational axis coinciding with said rotational axis of said gantry.

6. A computed tomography apparatus as claimed in claim 1 wherein said curved solid-state radiation detector is mountable in said gantry to be movable into said beam path by displacement parallel to a rotational axis of said gantry.

7. A computed tomography apparatus as claimed in claim 1 wherein said curved solid-state radiation detector is movable along a motion direction into said beam path and has a front edge which enters first into said beam path, and wherein said computed tomography apparatus further comprises electronic components for driving and readout of pixels of said curved solid-state radiation detector, said electronic components being mounted at edges of said curved solid-state radiation detector other than said front edge.

8. A computed tomography apparatus as claimed in claim 1 further comprising a control device disposed remote from said curved solid-state radiation detector, and further comprising a wireless signal transmission system for transmitting signals picked up by said solid-state radiation detector to said control device and for transmitting control signals from said control device to said curved solid-state radiation detector.

9. A computed tomography apparatus as claimed in claim 8 wherein said wireless transmission system is selected from the group consisting of optical transmission systems and electromagnetic transmission systems.

10. A computed tomography apparatus as claimed in claim 8 wherein said wireless transmission system is an infrared transmission system.

11. A computed tomography apparatus as claimed in claim 8 wherein said wireless transmission system is an antenna system.

12. A computed tomography apparatus as claimed in claim 1 further comprising a control device disposed remote from said curved solid-state radiation detector, and a stationary wiper ring and a plurality of wiper contacts interacting with said stationary wiper ring for transmitting signals picked up by said curved solid-state radiation detector to said control device and for transmitting control signals from said control device to said curved solid-state radiation detector.

13. A computed tomography apparatus as claimed in claim 1 further comprising a radiation diaphragm allocated to said x-ray source in said beam path for varying a size of a radiation field of said x-ray beam.

14. A computed tomography apparatus as claimed in claim 13 further comprising a control device for operating said diaphragm to vary said size of said radiation field.

15. A computer tomography apparatus as claimed in claim 1 further comprising a control device connected to said x-ray source for controlling said x-ray source independently of whether said x-ray beam is incident on said x-ray detector or said curved solid-state radiation detector.

* * * * *